(12) United States Patent
Pelletier et al.

(10) Patent No.: US 6,901,280 B2
(45) Date of Patent: *May 31, 2005

(54) EVALUATING DISEASE PROGRESSION USING MAGNETIC RESONANCE IMAGING

(75) Inventors: Jean Pierre Pelletier, Saint-Lambert (CA); Johanne Martel-Pelletier, Saint-Lambert (CA); M. Jacques de Guise, Montreal (CA); Jean-Pierre Raynauld, Boucherville (CA); Marie-Josee Barthiaume, Ville Mont-Royal (CA); Gilles Beaudoin, St. Lambert (CA); M. Benoit Godbout, Montreal (CA); M. Claude Kauffmann, Montreal (CA)

(73) Assignee: Arthrovision, Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/430,800

(22) Filed: May 6, 2003

(65) Prior Publication Data

US 2004/0015072 A1 Jan. 22, 2004

Related U.S. Application Data

(63) Continuation of application No. 09/704,269, filed on Nov. 1, 2000, now Pat. No. 6,560,476.
(60) Provisional application No. 60/162,871, filed on Nov. 1, 1999.

(51) Int. Cl.[7] ................................................ A61B 5/05
(52) U.S. Cl. ........................ 600/410; 600/415; 382/130
(58) Field of Search ................................ 600/410, 415; 382/130, 415, 132, 151, 128, 194, 294; 128/920, 922

(56) References Cited

U.S. PATENT DOCUMENTS

| 5,007,425 A | 4/1991 | Vanek et al. ................. 128/653 |
| 5,071,602 A | 12/1991 | Nambu et al. ................. 264/28 |
| 5,351,006 A | 9/1994 | Sumanaweera et al. ..... 324/309 |

(Continued)

FOREIGN PATENT DOCUMENTS

| EP | 0 602 730 A2 | 6/1994 |
| WO | WO 97/06744 | 2/1997 |
| WO | WO 00/35346 | 6/2000 |

OTHER PUBLICATIONS

Andriacchi, Thomas P. et al., *Methods for Evaluation the Procession of Osteoarthritis*, Journal of Rehabilitation Research and Development, vol. 37, No. 2, Mar./Apr. 2000, pp. 163–170.

(Continued)

*Primary Examiner*—Quang T. Van
(74) *Attorney, Agent, or Firm*—Kristofer E. Elbing

(57) ABSTRACT

An orthopedic magnetic resonance imaging system is disclosed. This system includes a source of magnetic resonance imaging data sets resulting from successive magnetic resonance imaging acquisitions from a diseased joint of a patient. A segmentation module segments surfaces in the joint based on information contained within at least one of the data sets, and a registration module spatially registers, in three dimensions, information represented by a first of the data sets with respect to information represented by one or more further data sets for the same patient. A comparison module detects differences between information represented by the data sets caused by progression of the disease in the joint of the patient between acquisitions. A cross-patient comparison module can compare detected differences for the patient with detected differences for at least one other patient.

16 Claims, 14 Drawing Sheets

U.S. PATENT DOCUMENTS

| | | | |
|---|---|---|---|
| 5,633,951 A | 5/1997 | Moshfeghi | 382/154 |
| 6,169,817 B1 | 1/2001 | Parker et al. | 382/131 |
| 6,310,619 B1 | 10/2001 | Rice | 345/420 |
| 6,373,249 B1 | 4/2002 | Kwok et al. | 324/306 |
| 6,560,476 B1 * | 5/2003 | Pelletier et al. | 600/410 |
| 2002/0087274 A1 | 7/2002 | Alexander et al. | 702/19 |
| 2002/0147392 A1 | 10/2002 | Steines et al. | 600/407 |
| 2002/0177770 A1 | 11/2002 | Lang et al. | 600/410 |
| 2002/0186818 A1 | 12/2002 | Arnaud et al. | 378/165 |

OTHER PUBLICATIONS

Wanschura, Thornsten et al., *Automatic Realignment of Time–Separated MR Images by Genetic Algorithm*, Magnetic Resonance Imaging, vol. 17, No. 2, 1999, pp. 313–317.

"A Method for Quantifying Time Dependent Changes In MR Signal Intensity of Articular Cartilage as a Function of Tissue Deformation in Intact Joints (Abstract)", Stammberger et al., Medical Engineering & Physics, vol. 20, No. 10, pp. 741–749, Dec. 1998.

"A Simple 2D Active Contour Model To Segment Non–Convex Objects In 3D Images", Benoit Godbout, Laboratoire D'Imagerie en Orthopedie, Hopital Notre–Dame, Montreal, 1998.

"Adaptive Template Moderated Spatially Varying Statistical Classification [of anatomy] (Abstract)", Warfield et al., Medical Image Computing and Computer–Assisted Intervention—MICCAI'98, First International Conference Proceedings p. 431–8, 1998.

"An Algorithmic Overview of Surface Registration Techniques for Medical Imaging", Michel A. Audette, et al., Medical Image Analysis 4, 2000.

"Automatic Realignment Of Time–Separated MR Images By Genetic Algorithm", Thorsten Wanschura, et al., Department Of Physics, University Of Exeter, UK, Feb. 1999.

"Automatic Segmentation and 3D–Registration of a Femoral Bone In MR Images Of The Knee", M. Wolf, et al., Pattern Recognition and Image Analysis, vol. 7, No. 1, 1997, pp. 152–165.

"Automatic Segmentation of MRI of the Knee", Simon Warfield et al., Proceedings of the International Society of Magnetic Resonance In Medicine, Apr. 18, 1998.

"Book Review: Musculoskeletal Imaging: Diagnostic and Therapeutic Procedures", Jacqueline C. Hodge, AJR, Mar. 1998.

"Cardiac MR Image Segmentation Using Deformable Models", A Gupta et al., IEEE, 1993.

"Computer–Aided Three Dimensional Assessment of Knee–Joint Cartilage with Magnetic Resonance Imaging" OJ Muensterer, et al., Clinical Biomechanics,Gb, Jul. 1, 1996.

"Creation And Smooth–Shading of Steiner Patch Tessela-tions", David E. Breen, Proceedings of the Fall Joint Computer Conference, Washington, Nov. 2, 1986.

"Deformable B–Solids and Implicit Snakes for 3–D Localization and Tracking of SPAMM MRI Data", Petia Radeva et al., Computer Vision And Image Understanding, May 1, 1997.

"Deformable Object Reconstruction With Particle Systems", Computers And Graphics, F. Jaillet et al., Jan., 1998.

"Deformation Analysis To Detect And Quantify Active Lesions In Three–Dimensional Medical Image Sequences", Jean–Philippe Thirion, et al., IEEE Transactions On Medical Imaging, May 5, 1999.

"Detecting Small Anatomical Change With 3D Serial MR Subtraction Images" M. Holden et al., Proceedings Of The Spie, Feb. 1999.

"Determination of 3D Cartilage Thickness Data from MR Imaging: Computational Method And Reproducibility In The Living", Tobias Stammberger, et al., Magnetic Resonance In Medicine, Mar. 1999.

"Effects of Sandimmune Neoral on Collagen–Induced Arthritis in DA Rats: Characterization By High Resolution Three–Dimensional Magnetic Resonance Imaging And By Histology", Nicolau Beckmann, et al., Journal Of Magnetic Resonance Academic Press, Mar. 1, 1998.

"Evaluation of Articular Cartilage Volume Quantification Following Registration of MR Images in the Knee (Abstract)", Jenny Zhao, Arthritis & Rheumatism 41 (9 SUPPL.), p S144, Sep. 1998.

"Fast Automated Segmentation And Visualization Methods for MR Images of the Knee Joint in Arthritis", R.I. Kitney et al., Department of Biological and Medical Systems, Imperial College, London, 1998.

"High–Resolution Three–Dimensional Magnetic Resonance Imaging for the Investigation of Knee Joint Damage During the Time Course of Antigen–Induced Arthritis In Rabbits", Janet Dawson et al., Arthritis and Rheumatism vol. 42, No. 1, Jan. 1999.

"In Vivo Reproducibility of Three–Dimensional Cartilage Volume and Thickness Measurement with MR Imaging", Felix Eckstein et al., AJR, Mar. 1998.

"Knee Cartilage Topography, Thickness, and Contact Areas from MRI: In–Vitro Calibration and In–Vivo Measurements", Cohen et al., Journal of the OsteoArthritis Research Society International, vol. 7, No. 1, 1999.

"Magnetic Resonance Image Segmentation Using Pattern Recognition, And Applied To Image Registration And Quantitation", N. Seed, Nmr In Biomedicine, London, UK, May 4, 1998.

"Magnetic Resonance Methods for Measurement of Disease Progression in Rheumatoid Arthritis" John C. Waterton, Magnetic Resonance Imaging, 1993.

"Magnetic Susceptibility in the Vertebral Column", Fritz Schick et al., Journal Of Magnetic Resonance. Series B, 1994.

"Measurement of Hippocampal Volume Changes in Serial MRI Scans" J.A. Schabel et al., Proceedings Of The Spie, 1999.

"Measurement of Localized Cartilage Volume and Thickness of Human Knee Joints by Computer Analysis of Three–Dimensional Magnetic Resonance Images", Ashwini A. Kshirsagar et al., Investigative Radiology, May 1998.

"MR Protocols for Imaging the Guinea Pig Knee" Paul J. Watson et al., Laboratory for Medicinal Chemistry, Cambridge University, May 5, 1997.

"Quantitation of Articular Cartilage Dimensions by Computer Analysis of 3D MR Images of Human Knee Joints", A. Kshirsagar, et al., Herchel Smith Laboratoiy For Medicinal Chemistry, University Of Cambridge, Nov. 2, 1997.

"Recurrent Nasal Tumor Detection by Dynamic MRI", Wen–Chen Huang et al., IEEE Engineering in Medicine and Biology, Jul./Aug. 1999.

"Smooth Surface Approximation To Serial Cross–Sections" Hyungjun Park et al., Computer Aided Design, Elsevier Publishers Bv., Barking, Gb, Dec. 1996.

"Surface–Based Labeling Of Cortial Anatomy Using A Deformable Atlas" Stephanie Sandor et al., IEEE Transactions On Medical Imaging, Feb. 1, 1997.

"Three–Dimensional Thickness and Volume Measurements of Knee Joint Cartilage with MRI: Validation in Anatomical Specimens via CT Arthrography (Abstract)", Schnier et al., Rofo–Fortschritte Auf Dern Gebiet Der Rontgenstrahlen und der Bildgebenden Verfahren, vol. 167, No. 5, 1997.

"Two Methods For Semi–Automated Quantification of Changes In Ventricular Volune and their Use in Schizophrenia" Nadeem Saeed, et al., Magnetic Resonance Imaging, 1998.

"Using Groups of 2D–Active Shape Models for 3D Segmentation of Femoral Anicular Cartilage" S Solloway et al., Departments of Medical Biophysics and Radiology, University of Manchester, 1998.

* cited by examiner

EVALUATING DISEASE PROGRESSION USING MAGNETIC RESONANCE IMAGING

This application is a continuation of U.S. Ser. No. 09/704,269, filed Nov. 1, 2000, U.S. Pat. No. 6,560,476 which claims the benefit of U.S. Provisional Application No. 60/162,871, filed Nov. 1, 1999, both of which are herein incorporated by reference.

FIELD OF THE INVENTION

This invention relates to methods and apparatus for tracking disease progression using magnetic resonance imaging, including methods and apparatus for efficiently and precisely tracking the progression of rheumatic diseases affecting cartilage.

BACKGROUND OF THE INVENTION

Osteoarthritis is a prevalent disease characterized mainly by cartilage degradation that is clinically reflected by a gradual development of joint pain, stiffness, and loss of motion. Osteoarthritis is extremely frequent in the general population, and it is estimated that its radiological prevalence is close to 50% overall. This figure is even higher in the elderly, with as much as 75% of the population between ages of 55 and 64 exhibiting some degree of radiological osteoarthritis in one or more joints. Although this disease is often benign, severe degenerative changes may cause serious disability.

Clinical osteoarthritis is now understood to be a complex interaction of degradation and repair of the cartilage, bone, and synovium, with secondary components of inflammation. The biochemical changes of osteoarthritis affect several cartilage components, including major matrix constituents, proteoglycans, and collagens. Decreased proteoglycan content in conjunction with damaged collagen structure leads to functional loss of normal matrix physiologic properties. Although the etiology of osteoarthritis is multiple and includes mechanical and biochemical factors, it appears that these culminate in an increased synthesis of proteolytic enzymes by the chondrocytes, which in turn leads to cartilage destruction.

There is no known cure for osteoarthritis, and current treatments are essentially limited to reliving the patient's symptoms. Research is under way, however, to find a therapeutic agent that will slow or stop the progression of the disease. One current approach to developing pharmacological treatments for osteoarthritis focuses on subchondral bone sclerosis, which is a well-recognized manifestation of osteoarthritis that could play a major role in the onset and/or progression of the disease.

Unfortunately, evaluating the efficacy of such agents is not an easy, straightforward process. For many years, studies of drug interventions on symptomatic knee osteoarthritis focused only on clinical parameters like pain and joint function, without assessing the anatomical impact of the disease (i.e., cartilage degradation and bone sclerosis). Simple radiographs are now often used in clinical trials for osteoarthritis to establish inclusion criteria, but such trials have not employed them to assess disease progression. More complex radiographic methods have also been proposed for measuring joint space width, such as the Buckland-Wight method, which may be used in clinical trials. Arthroscopy appears reliable and sensitive to changes, but it only allows for evaluation of the cartilage surface. It also appears to be somewhat subjective even when independently trained evaluators review video recordings of the procedures, and, above all, it is invasive.

A number of academic researchers have evaluated the use of Magnetic Resonance Imaging (MRI) for orthopedic investigations over the last ten years. Some researchers have proposed using MRI to reproducibly quantify articular dimensions to follow disease progression, and thereby assess whether proposed treatments may be responsible for changing the rate of cartilage loss. But the actual application of these proposed systems to the complex problem of making meaningful measurements on acutal diseased joints has not been shown to be entirely successful. This may be due to one or more of a variety of shortcomings, including extensive manual treatment and interpretation of data, excessive reliance on subjective human judgment, insufficient accuracy or repeatability to achieve meaningful results when used on actual diseased joints, inability to distinguish secondary symptoms, and/or excessively long scan times.

SUMMARY OF THE INVENTION

Several aspects of the invention are presented in this application. These relate to methods and apparatus for tracking disease progression using magnetic resonance imaging, including methods and apparatus for efficiently and precisely tracking the progression of rheumatic diseases affecting cartilage.

In one general aspect, the invention features an orthopedic magnetic resonance imaging system that includes a source of magnetic resonance imaging data sets resulting from successive magnetic resonance imaging acquisitions from a diseased joint of a patient. A segmentation module is responsive to the source of magnetic resonance imaging data sets and operative to segment surfaces in the joint based on information contained within at least one of the data sets. A registration module is responsive to the source of magnetic resonance imaging data sets and operative to spatially register, in three dimensions, information represented by a first of the data sets with respect to information represented by one or more further data sets for the same patient. A comparison module is responsive to the registration module and operative to detect differences between information represented by the data sets caused by progression of the disease in the joint of the patient between acquisitions.

In preferred embodiments, the comparison module can be operative to detect changes in cartilage thickness within the joint. The comparison module can be operative to detect changes in cartilage volume within the joint. The comparison module can be operative to detect changes in characteristics of cartilage material within the joint, which can be reflected in changes in magnetic resonance signal from the cartilage material. The system can further include a cross-patient comparison module responsive to the comparison module to compare detected differences for the patient with detected differences for at least one other patient. The system can further include a multi-patient database with the cross-patient comparison module including a statistical analysis module operative to derive statistical information about the progression of disease in the joints of a number of patients. The registration module can be operative to spatially register the data sets to within an average RMS value of about 50 microns, or even 10 microns. The registration module can include an automatic registration module operative to perform at least a three-dimensional preliminary spatial registration independent of user input. The registration module can be operative to perform the registration based on previously acquired magnetic resonance imaging data for the same patient. The segmentation module can be an automatic segmentation module responsive to the source of magnetic resonance imaging data sets and operative to automatically segment anatomical features in the patient with substantially only supervisory and artifact-correcting user input. The source of magnetic resonance imaging data can be operative to provide data sets optimized for the detection of at least bone and cartilage. The source of magnetic resonance imaging data can include a magnetic resonance imaging system operative to acquire the data sets using a sequence which is less than about 30 minutes in duration. The source of magnetic resonance imaging data sets can include a magnetic resonance imaging system and a support assembly operative to immobilize the diseased joint within the magnetic resonance imaging system with the joint at a predetermined three-dimensional position. The magnetic resonance imaging system can include a knee coil with the support assembly including a heel constraint and at least two flexible wedges that are each operative to interact with a leg of the patient and the knee coil. The support assembly can be operative to repeatedly immobilize the joint at predetermined three-dimensional positions that fall within a range of less than 17 or even 7 millimeters along the longitudinal axis of the magnetic resonance imaging system. The system can further include a differential display module operative to generate a difference map depicting differences between the data sets detected by the comparison module. The joint can be a load-bearing joint, with the imaging data sets include imaging data for at least the majority of the load bearing surfaces of the joint. The segmentation module can employ an active contour algorithm. The active contour algorithm can be a subpixel active contour algorithm. The segmentation module can employ an active contour algorithm configured to segment open contours with minimal operator intervention. The segmentation module can employ a three-dimensional gradient-driven active contour algorithm. The comparison module can be operative to detect differences between information represented by the data sets within one or more sub-regions of a surface of the joint caused by progression of the disease in the joint of the patient between acquisitions. The sub-regions can be based on polar coordinates or Cartesian coordinates.

In another general aspect, the invention features a method of monitoring disease progression in a joint that includes obtaining successive images of a same joint for each of a plurality of patients, where at least some of the joints are diseased. The method also includes the steps of segmenting joint surfaces within at least one of the images for each patient, and, for each of the patients, spatially registering joint features for one of the successive images with another of the successive images. Differences are detected between the registered successive images for each of the individual patients, and the differences are compared for different ones of the patients.

In preferred embodiments, the method can further include the step of administering a therapeutic agent to at least some of the patients before the acquisition of at least some of the successive images, and evaluating the differences between the registered successive images to obtain a measure of the efficacy of the therapeutic agent. The method can further include the step of evaluating the differences between the registered successive images to determine how to treat individual ones of the patients. The therapeutic agent can be designed to treat rheumatic diseases affecting the cartilage. The step of obtaining can include performing a magnetic resonance imaging acquisition and can further include the step of immobilizing the diseased joint with the joint at a predetermined flexion angle during the step of performing a magnetic resonance imaging acquisition. The step of obtaining can include performing a magnetic resonance imaging acquisition and further include the step of completely immobilizing the diseased joint with the joint at a predetermined three-dimensional position during the step of performing a magnetic resonance imaging acquisition. The step of immobilizing can be operative to repeatedly immobilize the joint at predetermined three-dimensional positions that fall within a range of less than 17 or even 7 millimeters along the longitudinal axis of the magnetic resonance imaging system used to perform the magnetic resonance imaging acquisition. The step of obtaining can include performing a magnetic resonance imaging acquisition, a step of positioning one or more markers proximate the joint during the magnetic resonance imaging, and a step of evaluating image distortion for the joint based on acquired image data for the markers. The step of obtaining can include performing a magnetic resonance imaging acquisition, a step of positioning one or more markers proximate the joint during the magnetic resonance imaging, and further including a step of evaluating patient movement artifact for the joint based on acquired image data for the marker. The step of positioning can position a pair of cylinders in orthogonal locations proximate the joint. The steps of detecting differences and comparing the differences can be operative to detect differences between information represented by the data sets within one or more sub-regions of a surface of the joint. The sub-regions can be based on polar coordinates or Cartesian coordinates.

In a further general aspect, the invention features an orthopedic magnetic resonance imaging system that includes means for obtaining successive images of a same joint for each of a plurality of patients, wherein at least some of the joints are diseased. Also included are means for segmenting joint surfaces within at least one of the images for each patient, means for spatially registering joint features for one of the successive images with another of the successive images for each of the patients, means for detecting differences between the registered successive images for each of the individual patients, and means for comparing the differences obtained for different ones of the patients.

In another general aspect, the invention features an orthopedic magnetic resonance imaging system that includes a source of magnetic resonance imaging data resulting from magnetic resonance imaging acquisitions from a diseased joint of a patient. The system also includes a segmentation module that is responsive to the source of magnetic resonance imaging data and to segmentation result storage, and that is operative to detect a boundary between two anatomical features of the joint in three dimensions based on both three-dimensional information from the diseased joint of the patient and prior segmentation results stored in the segmentation result storage.

In preferred embodiments, the system can further include a registration module responsive to the source of magnetic resonance imaging data and operative to spatially register three-dimensional image data from a first acquisition for the patient and three-dimensional image data from a later acquisition for the same patient.

In a further general aspect, the invention features a method of monitoring disease progression in a joint that includes obtaining a first magnetic resonance imaging data set resulting from magnetic resonance imaging acquisition of a joint of a patient, segmenting a boundary between two anatomical features of the joint based on the first magnetic resonance imaging data set, and saving segmentation information derived during the step of segmenting. A second magnetic resonance imaging data set resulting from a magnetic resonance imaging acquisition of the same joint for the same patient is then obtained, and the boundary between the same two anatomical features of the same joint of the same patient is segmented based on both the second magnetic resonance imaging data set and the segmentation information saved in the step of saving.

In preferred embodiments, the method can further include the step of administering a therapeutic agent for the disease to a plurality of patients, with the steps of obtaining, the steps of segmenting, and the step of saving being performed for a plurality of patients, and the method can further include the step of evaluating the effect of the therapeutic on the disease based on results of the steps of obtaining, the steps of segmenting, and the step of saving.

In another general aspect, the invention features an orthopedic magnetic resonance imaging system that includes means for obtaining a first magnetic resonance imaging data set resulting from magnetic resonance imaging acquisition of a joint of a patient and for obtaining a second magnetic resonance imaging data set resulting from a magnetic resonance imaging acquisition of the same joint for the same patient. Also included are means for segmenting a boundary between two anatomical features of the joint based on the first magnetic resonance imaging data set, means for saving segmentation information derived by the means for segmenting, and means for segmenting the boundary between the same two anatomical features of the same joint of the same patient based on both the second magnetic resonance imaging data set and the segmentation information saved by the means for saving.

In a further general aspect, the invention features an orthopedic magnetic resonance imaging system that includes a source of magnetic resonance imaging data resulting from magnetic resonance imaging acquisitions from a diseased joint of a patient, and a segmentation module that is responsive to the source of magnetic resonance imaging data sets and is operative to detect a boundary between two anatomical features of the joint in three dimensions by detecting an outline in each of a plurality of at least generally parallel planes within the volume, wherein the outline in at least some of the planes is based on data from at least one other of the planes.

In another general aspect, the invention features a method of monitoring disease progression in a joint that includes obtaining a first magnetic resonance imaging data set resulting from magnetic resonance imaging acquisition of a joint of a patient, and segmenting an outline of a boundary between two anatomical features of the joint of the patient in three dimensions by detecting an outline in each of a plurality of at least generally parallel planes within the volume, wherein the outline in at least some of the planes is based on data from at least one other of the planes.

In a further general aspect, the invention features an orthopedic magnetic resonance imaging system that includes means for obtaining a first magnetic resonance imaging data set resulting from magnetic resonance imaging acquisition of a joint of a patient, and means for segmenting an outline of a boundary between two anatomical features of the joint of the patient in three dimensions by detecting an outline in each of a plurality of at least generally parallel planes within the volume, wherein the outline in at least some of the planes is based on data from at least one other of the planes.

In another general aspect, the invention features a magnetic resonance imaging system that includes a source of magnetic resonance imaging data resulting from magnetic resonance imaging acquisition from an imaging volume for a patient, a fitting module operative to fit a biparametric surface to an anatomical feature described by the data for the patient, and a projection module responsive to the magnetic resonance imaging data source and operative to project at least a portion of the data representing the three-dimensional anatomical feature onto the biparametric surface.

In preferred embodiments, the surface can be a biparametric surface having a three-dimensional topology. The system can further include a display module responsive to the projection module to display the two dimensional surface on a planar display. The anatomical feature can include at least the condyles of the femur with the surface being a cylinder. The anatomical feature can include at least the plateau regions of the tibia and wherein the surface is a plane. The anatomical feature can include at least the posterior surface of the patella and wherein the surface is a cylinder. The system can further include means for performing image manipulations on data representing the two dimensional surface. The system can further include a repositioning module operative to user input to project the three-dimensional anatomical feature onto a further biparametric surface layers proximate the biparametric surface. The system can further include an inter-patient comparison module responsive to the projection module to compare results derived from the projections from the projection module for a plurality of different patients. The system can further include a display module responsive to the inter-patient comparison module to display comparison information for the projections.

In a further general aspect, the invention features a magnetic resonance imaging method that includes obtaining a magnetic resonance imaging data set resulting from a magnetic resonance imaging acquisition from an imaging volume for a patient, fitting a biparametric surface to an anatomical feature described by the data set for the patient, and projecting at least a portion of the data representing the three-dimensional anatomical feature onto the biparametric surface.

In preferred embodiments, the method can further include repeating the steps of obtaining, fitting, and projecting for a plurality of different patients, and can further include the steps of comparing resulting projections for the plurality of different patients.

In another general aspect, the invention features a magnetic resonance imaging system that includes means for obtaining a magnetic resonance imaging data set resulting from a magnetic resonance imaging acquisition from an imaging volume for a patient, means for fitting a biparametric surface to an anatomical feature described by the data set for the patient, and means for projecting at least a portion of the data representing the three-dimensional anatomical feature onto the biparametric surface.

In a further general aspect, the invention features a phantom for a magnetic resonance imaging system that includes a body defining a first cavity for holding a first material that has at least one magnetic resonance property that is substantially similar to that of cartilage, and a second cavity for holding a second material that has at least one magnetic resonance property that is substantially similar to that of an anatomical feature that is adjacent to cartilage.

In preferred embodiments, the cavities can be on the order of the thickness of joint features to be imaged using magnetic resonance imaging. The cavities can be on the order of 0.125 inches thick. The body can define a first partition separating the first and second cavities. The partition can be on the order of less than 100 microns thick. The body can further define a third cavity for holding a third material, with the body including a second partition separating the second and third cavities.

In another general aspect, the invention features a magnetic resonance imaging method that includes obtaining and processing a magnetic resonance image of a phantom of known geometry that simulates the contrast level between cartilage and at least one anatomical feature adjacent to cartilage, obtaining a magnetic resonance image of a joint of a patient, and processing results of the step of obtaining a magnetic resonance image of a joint of a patient based on results of the step of obtaining and processing a magnetic resonance image of a phantom.

In preferred embodiments, the step of processing can be a step of verifying that results of the step of obtaining a magnetic resonance image of a joint of a patient fall within a predetermined contrast range based on results of the step of obtaining a magnetic resonance image of a phantom. The step of processing can be a step of correcting results of the step of obtaining a magnetic resonance image of a joint based on results of the step of obtaining an image of a phantom. The step of obtaining a magnetic resonance image of a phantom and the step of obtaining a magnetic resonance image of a joint can be performed using a first magnetic resonance imaging configuration, and the method can further include a further step of obtaining a magnetic resonance image of a phantom of known geometry that simulates the contrast level between cartilage and at least one adjacent anatomical feature and a further step of obtaining a magnetic resonance image of a joint of a patient. The step of obtaining a magnetic resonance image of a phantom can be performed for a first material that has at least one magnetic resonance property that is substantially similar to that of bone and a second material that has at least one magnetic resonance property that is substantially similar to that of cartilage. The step of obtaining a magnetic resonance image of a phantom can be performed for a phantom that includes volumes on the order of the volumes of joint features to be imaged using magnetic resonance imaging.

In a further general aspect, the invention features a phantom for a magnetic resonance imaging system that includes first means having at least one magnetic resonance property that is substantially similar to that of cartilage, and second means having at least one magnetic resonance property that is substantially similar to that of an anatomical feature that is adjacent to cartilage.

In another general aspect, the invention features a magnetic resonance imaging system that includes a source of three-dimensional magnetic resonance imaging data sets resulting from magnetic resonance imaging acquisition from a joint of a patient, a segmentation module that is responsive to the source of magnetic resonance imaging data sets and is operative to detect a boundary between two anatomical features of the joint in three dimensions based on three-dimensional information from a first of the data sets, and a comparison module responsive to the segmentation module and to a second of the data sets and operative to compare boundary surface data resulting from segmentation by the segmentation module for the first data set with volumetric data from the second data set.

In preferred embodiments, the comparison module can be included in a second segmentation module operative to segment the same boundary between the same anatomical features in the second data set. The comparison module can be included in a registration module operative to spatially register the boundary between the anatomical features segmented in the first data set with the second data set.

In a further general aspect, the invention features a magnetic resonance imaging method that includes obtaining a first three-dimensional magnetic resonance imaging data set resulting from magnetic resonance imaging acquisition from a joint of a patient, segmenting a boundary between two anatomical features of the joint of the patient based on the first magnetic resonance imaging data set, obtaining a second three-dimensional magnetic resonance imaging data set resulting from a magnetic resonance imaging acquisition of an imaging volume for the same joint of the same patient, and comparing surface data resulting from the step of segmenting with volumetric data resulting from the second data set.

In preferred embodiments, the step of comparing can be part of a step of segmenting the same boundary between two anatomical features of the patient based on the second magnetic resonance imaging data set. The step of comparing can be part of a second step of spatially registering the boundary between the anatomical features segmented in the first data set with the second data set.

In another general aspect, the invention features a magnetic resonance imaging system that includes means for obtaining a first three-dimensional magnetic resonance imaging data set resulting from magnetic resonance imaging acquisition from a joint of a patient, means for segmenting a boundary between two anatomical features of the joint of the patient based on the first magnetic resonance imaging data set, means for obtaining a second three-dimensional magnetic resonance imaging data set resulting from a magnetic resonance imaging acquisition from the same joint of the same patient, and means for comparing surface data resulting from the step of segmenting with volumetric data resulting from the second data set.

Systems and methods according to the invention are advantageous in that they can allow precise quantitative tracking of the progression of diseases, such as rheumatic diseases affecting the cartilage. Such precise quantitative tracking can allow for accurate evaluation of the effects of pharmaceutical agents on these diseases in clinical trials. It may also allow physicians to accurately determine how and when to treat individual patients.

Systems according to the invention may also provide more insight into disease progression. Because they allow physicians to view the effect of disease on different joint structures, systems according to the invention may permit physicians to gain a more detailed insight into the studied disease for a patient or group of patients. This may result in more finely targeted treatment research, or more effectively administered treatment delivery.

The benefits described above can be provided in a highly efficient manner. Because many aspects of systems and methods according to the invention are extensively automated, little operator intervention is necessary. And because such systems and methods are highly sensitive, relatively short follow-up periods may be achievable. These efficiencies can have a significant impact on the cost of large-scale clinical studies, where many patients must be carefully evaluated. These cost savings may result in the evaluation of a larger number of potential treatments.

DETAILED DESCRIPTION OF AN ILLUSTRATIVE EMBODIMENT

Figure 1:
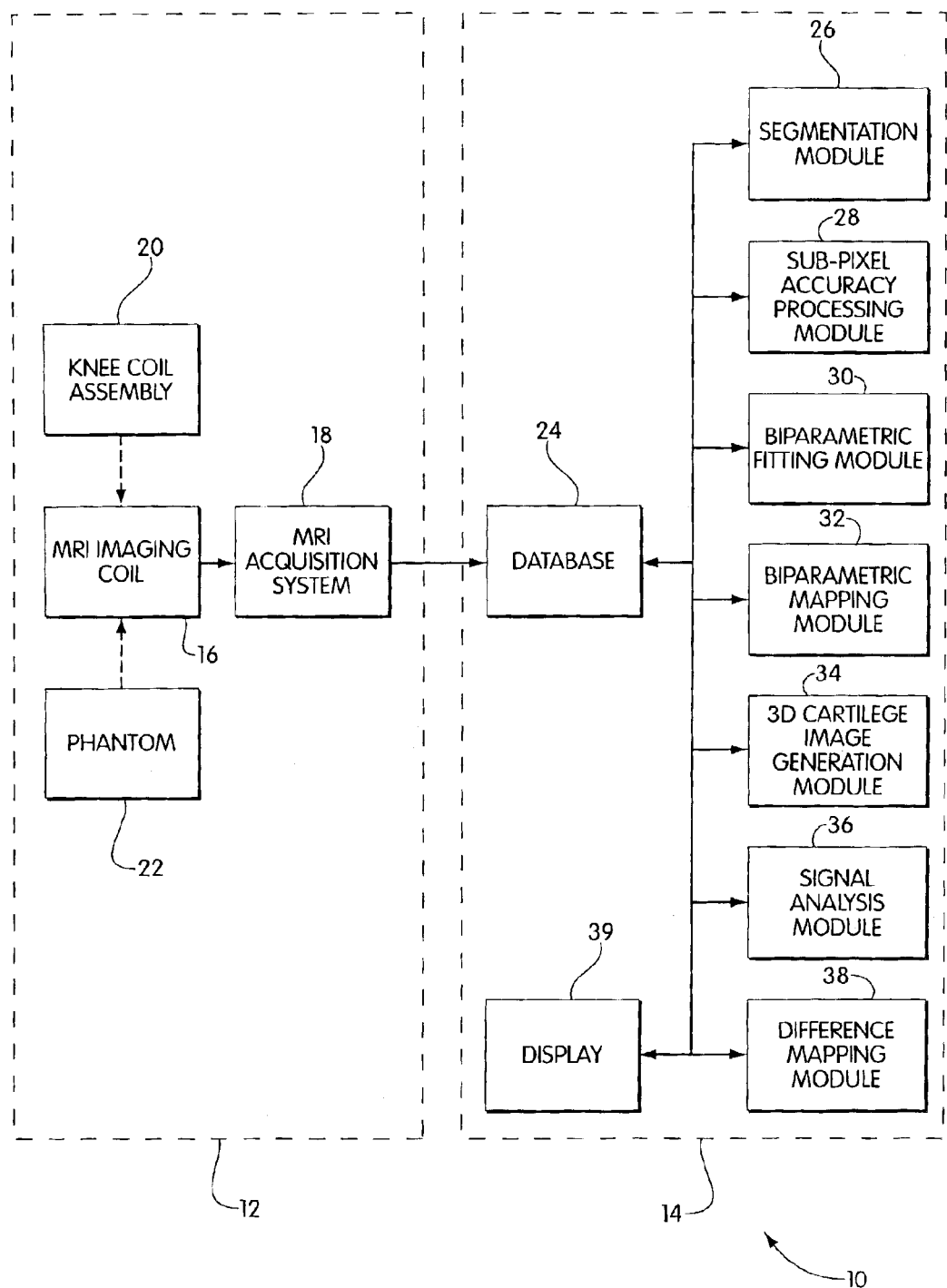
FIG. 1 is a block diagram of a disease progression monitoring system according to the invention configured for monitoring rheumatic diseases affecting cartilage.

Referring to FIG. 1, a disease progression monitoring system 10 according to the invention is configured for monitoring rheumatic diseases affecting cartilage in the knee. This system could also be configured to monitor disease progression in other joints in the body, such as the hip, or joints of the hands or spine. But the knee appears to be an appropriate choice for monitoring most rheumatic diseases affecting the cartilage, such as osteoarthritis. Because the knee usually bears a substantial load, it is believed that it tends to show arthritic symptoms at least as early as other joints, making it a good predictor of overall disease progression. And because of its relatively large size and accessibility, its internal surface can be more readily imaged and quantified than other joints.

The disease progression monitoring system 10 includes an acquisition subsystem 12 and a processing subsystem 14. The acquisition subsystem includes an MRI imaging coil 16 operatively connected to an MRI acquisition system 18. A knee coil assembly 20 that is compatible with the MRI imaging coil and a phantom 22 also form a part of the acquisition subsystem. The acquisition subsystem can include a commercially available 1.5 Tesla MRI imaging system, such as are available from Siemens AG of Munich, Germany. A suitable knee coil assembly is also available from Siemens.

The processing subsystem 14 includes a database 24 that is operatively connected to the MRI acquisition system. The operative connection between the MRI acquisition system and the database can take different forms, such as a network connection or a dedicated fiber-optic link. It may also take the form of an intermittent connection, such as an e-mail link, or a physically transported high-capacity storage medium, such as an optical disk. The database can range from a collection of files for smaller research systems to more powerful and feature-rich databases for systems configured to process data for larger numbers of patients. Also included in the processing system are a segmentation module 26, a sub-pixel processing module 28, a biparametric fitting module 30, a biparametric mapping module 32, a three-dimensional cartilage image gereration module 34, a signal analysis module 36, a difference mapping module 38, and a display 39. These can all be operatively connected to the database such that they can access raw data sets received from the acquisition subsystem 12, as well as different processed versions of these data sets. Each of these modules can be implemented using special-purpose hardware, software running on a general-purpose processor, or a combination of both. In addition, while the system can be broken into the series of modules shown in FIG. 1, one of ordinary skill in the art would recognize that it is also possible to combine them and/or split them to achieve a different breakdown. In one embodiment, the modules and database are part of a larger software system that runs on one or more workstation computers outfitted with an operating system such as Microsoft's Windows® 9X or Windows NT® operating system.

Figure 2:
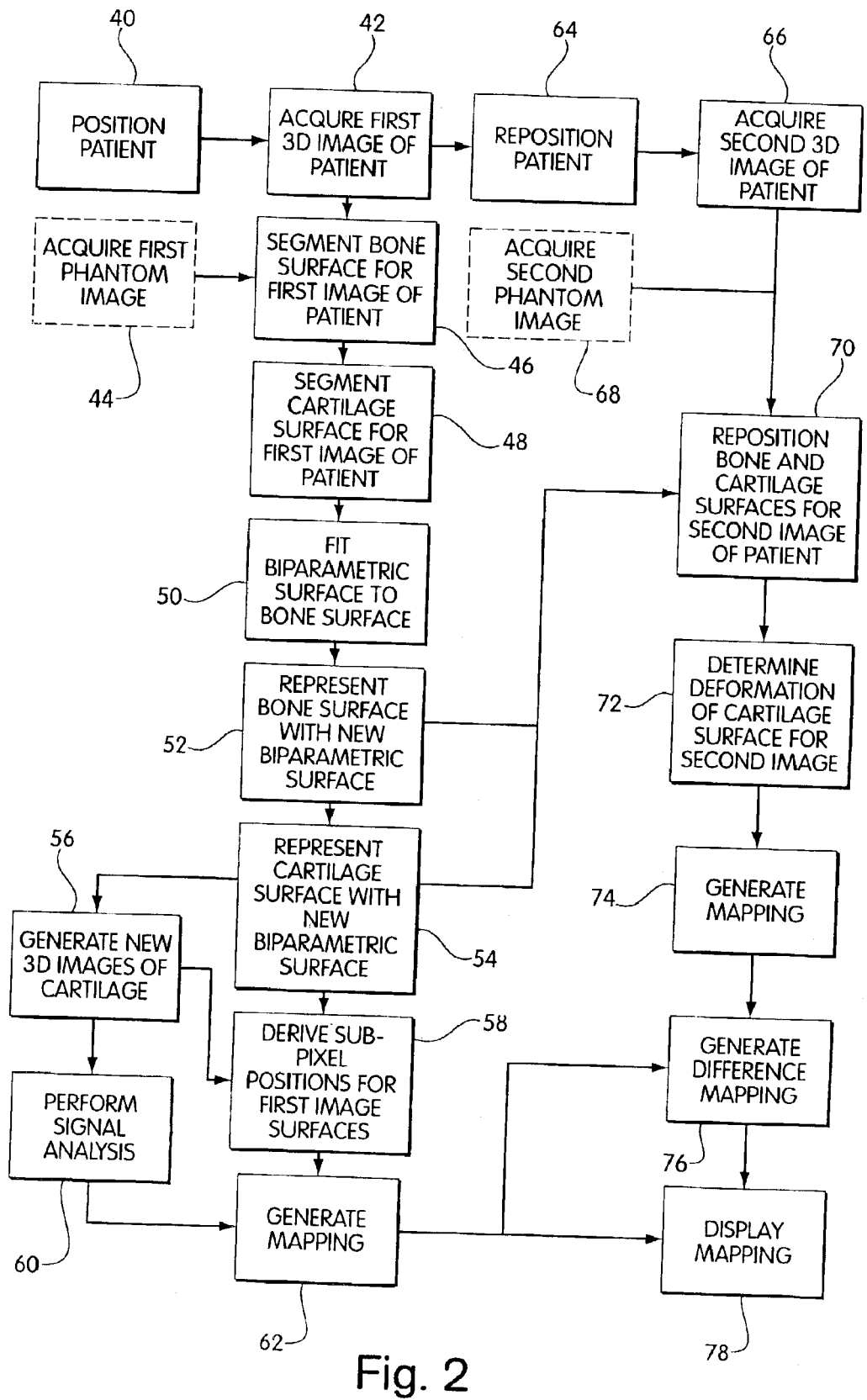
FIG. 2 is a flowchart illustrating the operation of the system of FIG. 1.
Figure 3:
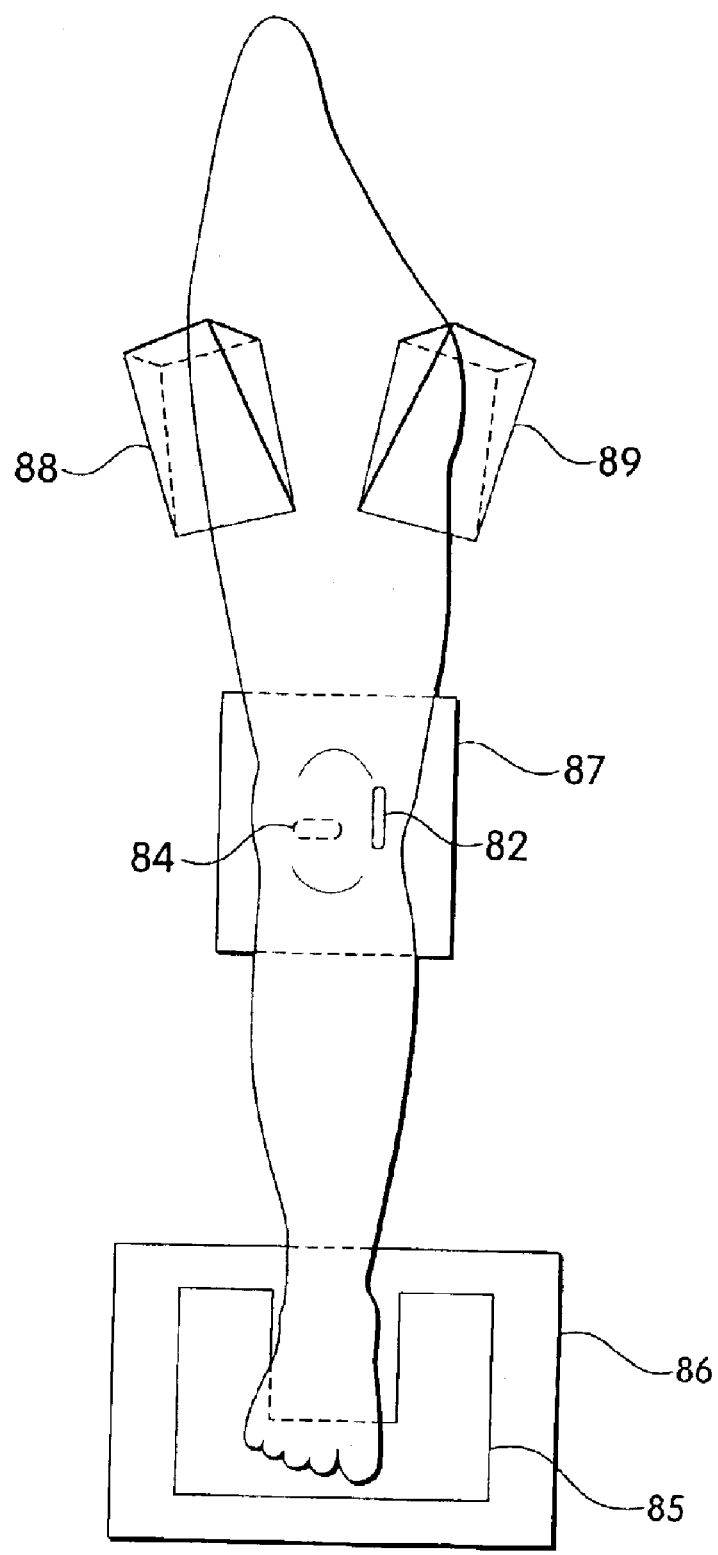
FIG. 3 is a schematic top view drawing illustrating general locations for the constraints and markers used in positioning of a patient's right knee in the system of FIG. 2.

In operation, referring to FIGS. 1–3, an MRI system operator begins by positioning the patient in the MRI coil 12 (step 40). This involves lying the patient generally in parallel with a longitudinal axis of the imaging coil and precisely positioning one of his or her legs comfortably bent within the imaging coil according to a defined positioning protocol. This protocol reproducibly positions the knee at a particular three-dimensional position with a predetermined degree of flexion. Use of the positioning protocol can be important in currently available systems to achieve images that are of a sufficient quality to be effectively processed by the processing system 14.

Figure 4:
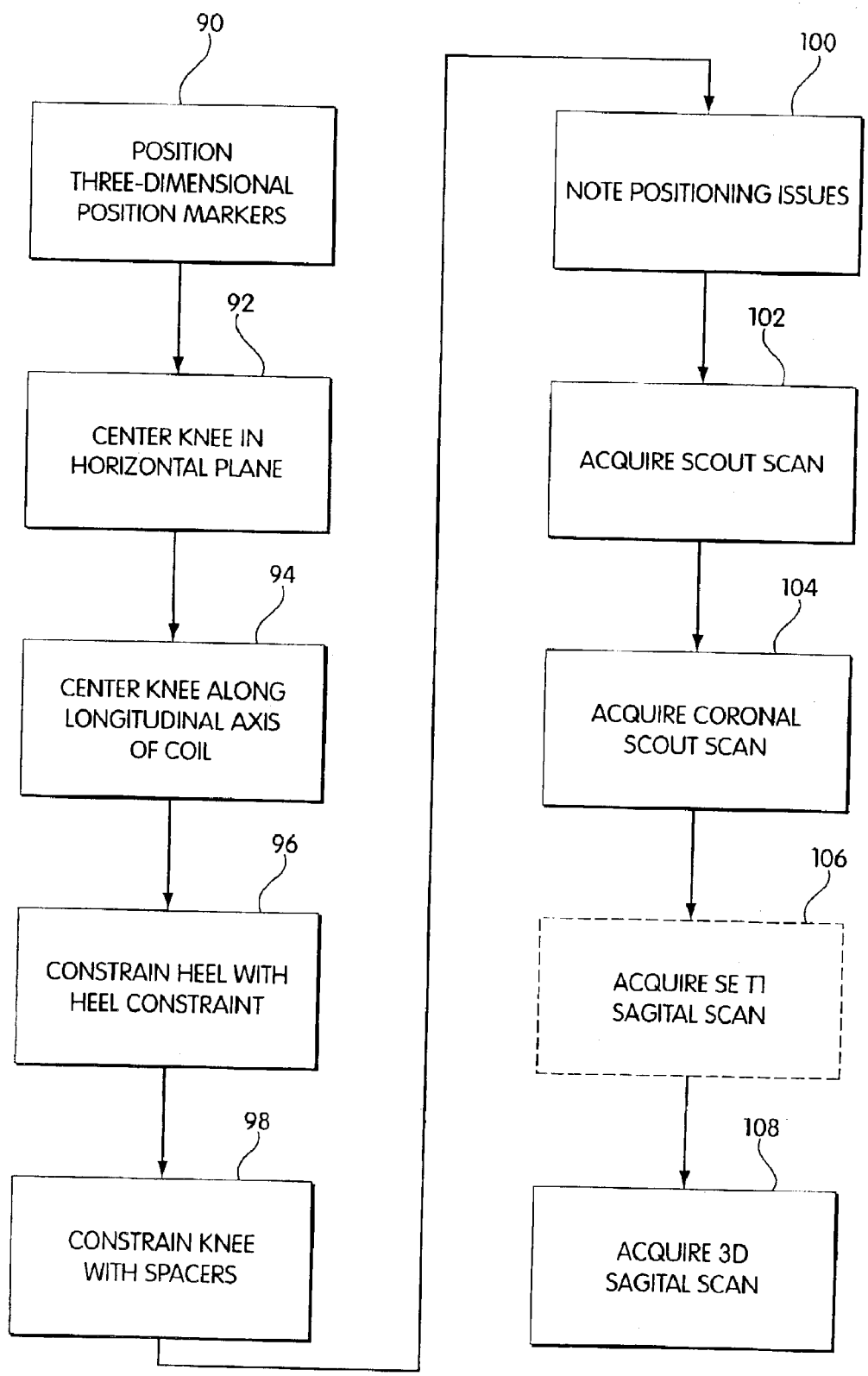
FIG. 4 is a flowchart illustrating the steps of a positioning protocol for the system of FIG. 2.

Referring to FIGS. 3 and 4, the positioning protocol includes first installing two three-dimensional markers 82 and 84 in generally orthogonal positions around the patient's knee (step 90). These markers are preferably cylindrical in shape and highly visible using the MRI protocol for imaging the knee. They provide reference data that can be used to detect any geometrical and signal drift in the data received from the MRI acquisition system, and to correct it if necessary. They also provide reference data that can be used to perform quality control analysis, such as if the patient moves during image acquisition. A first of the markers 82 is positioned next to the patient's patella on the inward side in a direction parallel to the longitudinal axis of the imaging coil. A second of the makers 84 is placed in the popliteal fossa in a generally horizontal plane. The markers can be implemented as hollow plastic tubes filled with $NiSO_4$ solution or vitamin E.

The patient's knee is next centered within a horizontal plane parallel to the longitudinal axis of the imaging coil (i.e., left-to-right—step 92). The rough line formed by the longitudinal axes of the femur and tibia is preferably centered as much as possible in this plane. The patient's patella is then centered along the longitudinal axis of the coil (step 94).

The positioned leg is constrained in place with a heel constraint and spacers. This process includes first constraining the heel with a commercially available heel constraint 85 and a foam spacer 86 to adjust its height (step 96). One or more foam spacers 87 are also placed beneath the small of the knee. Two wedge-shaped spacers 88 and 89 are then placed above the quadriceps to the left and right of the longitudinal axis of the imaging coil 16, and wedged in place within the knee coil 20 to hold the knee still (step 98). Any particular positioning issues are noted in the patient's record (step 100).

Once the patient's leg is positioned and constrained, the operator begins the process of acquiring a three-dimensional image of the patient's knee (step 42). He or she first instructs the MRI acquisition system 18 to acquire a scout scan of the knee from the MRI imaging coil 16 (step 102). The operator then instructs the MRI acquisition system to acquire a coronal scout scan based on the first scout scan (step 104). The image plane of this coronal scan is positioned at the center of the lower end of the femur, and is then backed up to the crossing point of the Bloomenstat line with the end of the anterior cruciate ligament. If necessary, the image plane is inclined to place it in alignment with the tibia, and this angle is noted in the patient's record. If this is the patient's first evaluation, the operator also acquires a short, standard SE T1 sagital scan (step 106), which will be used for anatomical evaluation. The final step in the protocol is to acquire a three-dimensional sagittal scan based on the coronal scout scan (step 108), and centered about the intercondylial notch (read-out along head-to-foot direction with resolution in the anterior-posterior axis reduced to 80% (NEX=0.8)).

Figure 5:
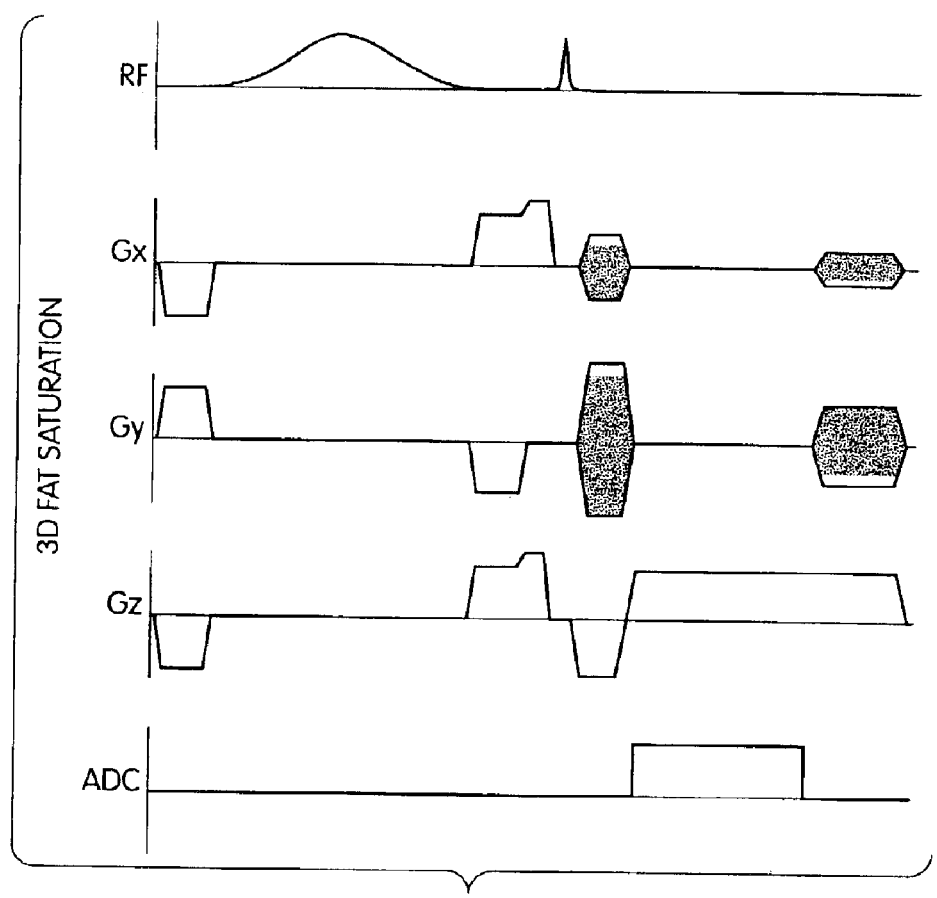
FIG. 5 is a waveform diagram illustrating the MRI sequence used by the system of FIG. 1 for one voxel in a slice.

Referring to FIG. 5, the acquisition follows a fat suppressed spoiled gradient echo sequence, which has been found to yield the best contrast for the interface between cartilage and the adjacent structures of the knee. It consists of 110 one mm thick partitions, obtained using a flip angle optimized for the Ernst angle of cartilage, which is about 20°. The Repetition Time (TR) is set to 42 ms, and the Echo Time (TE) is set to 7 ms. Each acquisition can cover a 308×512 or a 358×512 matrix over a rectangular 6/8 field of view (FOV) of 160 mm, and the overall acquisition time ranges from 20 to 30 minutes. The resulting effective voxel size is of 0.31×0.39×1.0 mm³. The imaging protocol may require a 220 hertz manual adjustment for very obese individuals, and the field of view may need to be enlarged for individuals with very large knees.

The chosen methodology represents an optimized compromise between cartilage contrast, 3D spatial resolution, maximization of signal/noise ratio, exposure time for the patient, and repeatability. The gradients are also optimised, with maximal slew rate and minimal gradient dwell time used throughout. Spoilers are minimised, as well. It is believed that the sequence should be transferable to other types of MRI machines.

The three-dimensional data set obtained is in the form of a series of sagittal image planes through the volume that surrounds the joint. It is stored permanently on a write-only optical disk, which is to be transferred to the database 24 in the processing subsystem 14. The particulars of patient positioning and imaging parameters are stored in a paper file to be kept at the imaging site.

Figure 6:
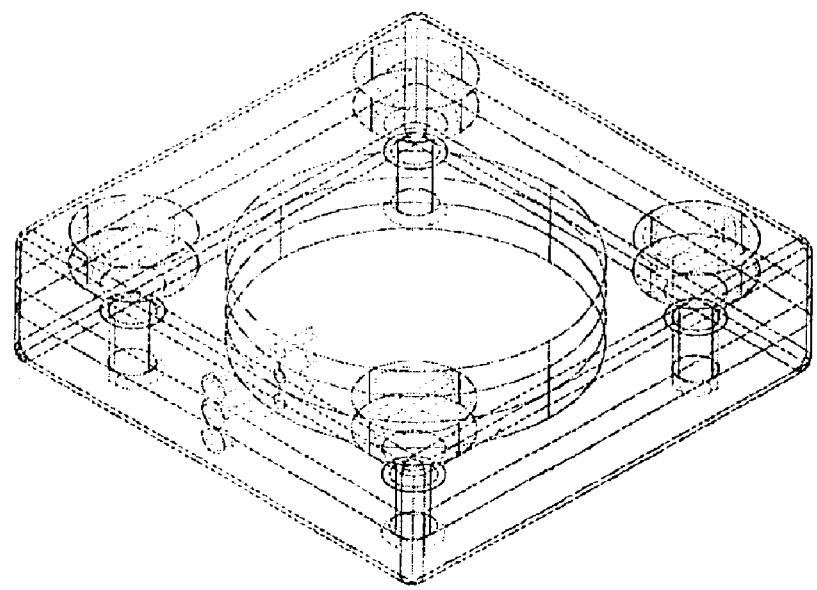
FIG. 6 is a perspective drawing illustrating a phantom for use with the system of FIG. 1.

Referring to FIG. 6, the system operator can also obtain an image of a phantom 110 (step 44). This image provides important information about the acquisition subsystem 12, which the processing subsystem can use to correct for variations in imaging parameters, such as may result from component drift or system repairs. The use of this phantom-based correction procedure can be particularly important in following rheumatic diseases, as successive scans of a same patient may be separated by several months, during which imaging conditions for a particular system may change. The phantom information may also be used to normalize data received from different systems. Note that phantom data may not need to be obtained each time a patient acquisition is performed, but can instead be obtained at regular intervals (e.g., weekly).

The phantom is designed to allow it to provide information about the MRI system's acquisition of known materials configured in a known geometry. The materials are selected to correspond to the different materials to be imaged. In the present embodiment, these are bone, cartilage, and synovial fluid. The phantom geometry is designed to position these materials relative to each other in ways that are comparable to the configuration of the target structures in the patient. The total volume and thickness of at least some of the materials is also designed to be comparable to that of the structures to be imaged.

A suitable phantom 110 can be constructed using as a structure that defines three closely-spaced, refillable, cylindrical chambers 112, 114, and 116. These chambers can be defined by a stack of three hollowed-out plates 118, 120, and 122 separated by thin sheets 124 and 126, and screwed together by screws 128, 130, 132, and 134 at its four corners. In one embodiment, each plate is a square Lexan® plate that defines a cylindrical space measuring 0.125 inches in height by 1.5 inches in diameter. The top and bottom plates are partially hollowed out to act as caps, and the central plate is bored through. The first sheet 124, which is 50 microns thick, separates the top plate 118 and the middle plate 120. The second sheet 126, which is of the same thickness, separates the middle plate 120 and the bottom plate 122. Between each chamber and one of the edges of the plates is a fill hole measuring 0.063 inches in diameter.

Once a three-dimensional data set from the patient and phantom data for the acquisition system have been obtained and transferred to the database 24, segmentation of the data can begin. Segmentation is the process of detecting edges of anatomical surfaces represented in the data contained in the data set for the patient. Segmentation begins for the bone surface (step 46) and then proceeds to the cartilage surface (step 48). This and subsequent operations can be performed for the end of one or more of the bones in the joint, such as the femur, tibia, and/or patella of the knee.

Figure 7:
FIG. 7 is a copy of an image of a sagittal slice from a data set acquired using the system of FIG. 1.

Referring to FIG. 7, the segmentation module 26 processes the patient's first data set to determine the outline of the bone extremities and the outline of the cartilage in each of the MRI slices. The operator begins by manually delineating the bone-cartilage interface on a first of the slices, being careful to avoid obvious artifacts. An active contour algorithm is then applied to the manual contours, and this process causes the contours to more closely define the outline of the bone-cartilage interface. In each subsequent slice, the contours from the previous slice are used to initialize the current slice. The active contour algorithm is described in "Simplified Active Contour Model Applied To Bone Structure Segmentation In Digital Radiographs," by C. Kauffmann, B. Godbout, and J. A. de Guise, Medical Imaging 1998, Proceedings of SPIE, Image Processing, 21–27, Feb. 1998; "Simple 2D active contour model to segment non-convex objects in 3D images," by B. Godbout, C. Kauffmann, and J. A. de Guise, Vision Interface, '98, SFU Harbour Center, Vancouver, British Colombia, Canada, 18–20, Jun., 1998; and "Segmentation d'Images Tridimensionelles à l'Aide de Contours Actifs Simplifiés," by Benoit Godbout (Engineering Master's Thesis), Ecole Technique Supérieure, Montréal, December 1997; which are all herein incorporated by reference.

The segmentation module then segments the cartilage-synovium interface (step 48). This process proceeds in the same manner as it did with the bone-cartilage interface. A skilled professional, such as a radiologist generally reviews results of the segmentation processes to make sure that artifacts have not introduced errors in the images.

Figure 8:
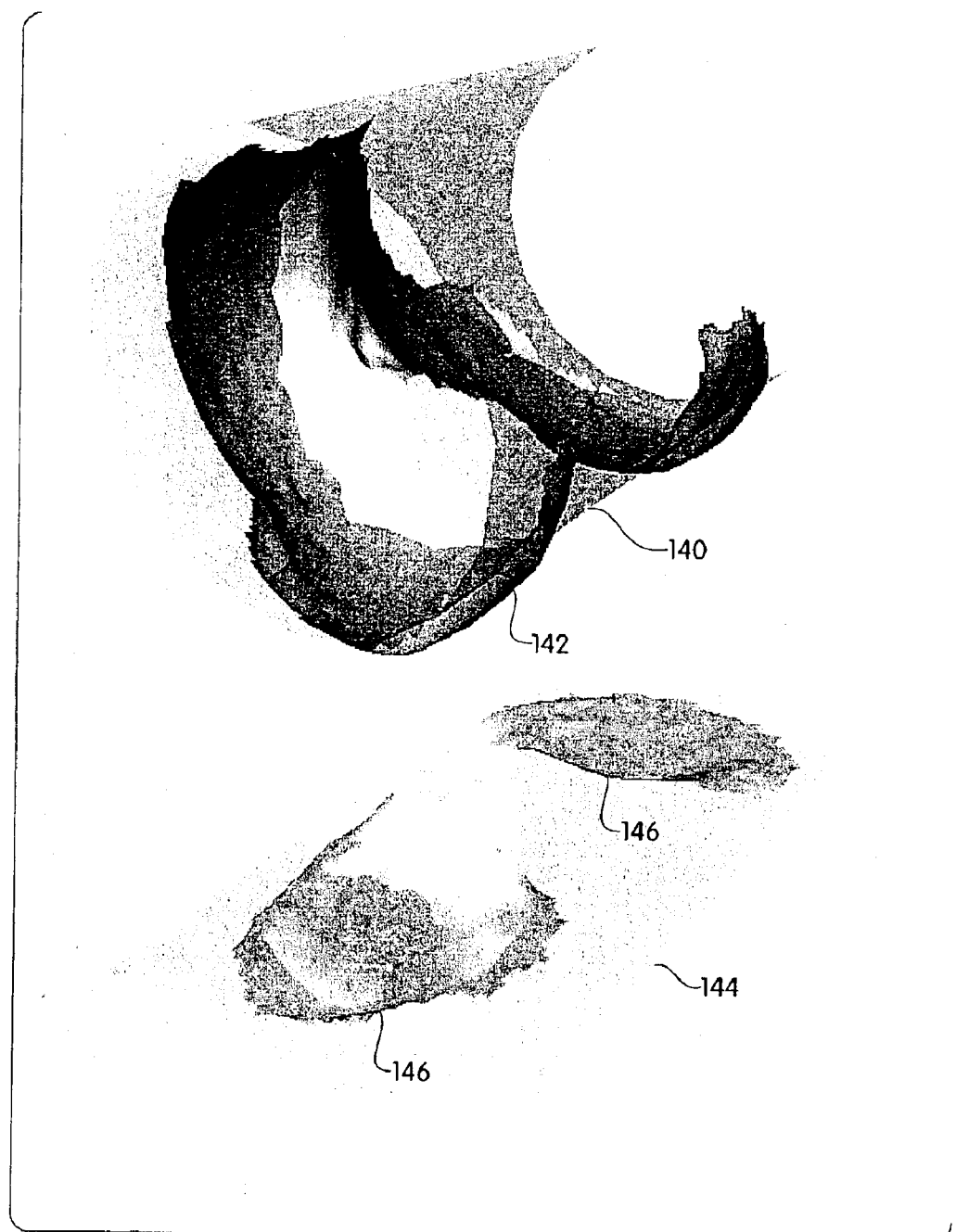
FIG. 8 is a three-dimensional drawing illustrating the fitting by the system of FIG. 1 of a biparametric surface of a three-dimensional geometrical primitive on bone surfaces for a femoral bone and a tibial bone.

Referring to FIG. 8, once the data set has been segmented, the system fits (step 50) a simple geometrical primitive to the 3D active contour results from the bone-cartilage interface. The primitive is chosen to mimic the shape of the bone surface. A cylinder is used for the femur and planes are used for the tibia and patella.

The fitting algorithm performs an iterative search for the best transformation in order to minimize the squared distance between the transformed contour points and a normalized geometrical primitive centered at the origin. To fit a cylinder, transformation parameters are two rotations around orthogonal axis (principal axis), two translations (position) and a scaling factor (radius). To fit a plane, the transformation parameters are two rotations around orthogonal axis (normal) and one translation (position).

A grid is defined on the fitted biparametric primitive surface in order to derive a new representation for the contour points. All contour points are first orthogonally projected on the grid surface. Each three-dimensional contour point ($x_i$, $y_i$, $z_i$) in the imaging coordinate system is mapped to a corresponding coordinate on the grid (column, row, offset). The result can be seen as an offset map where the pixel intensity is a distance to the primitive.

Figure 9A:
FIGS. 9(a) and 9(b) are images of a biparametric surface of the same bone surface shown in FIG. 8 before and after interpolation.
Figure 9B:
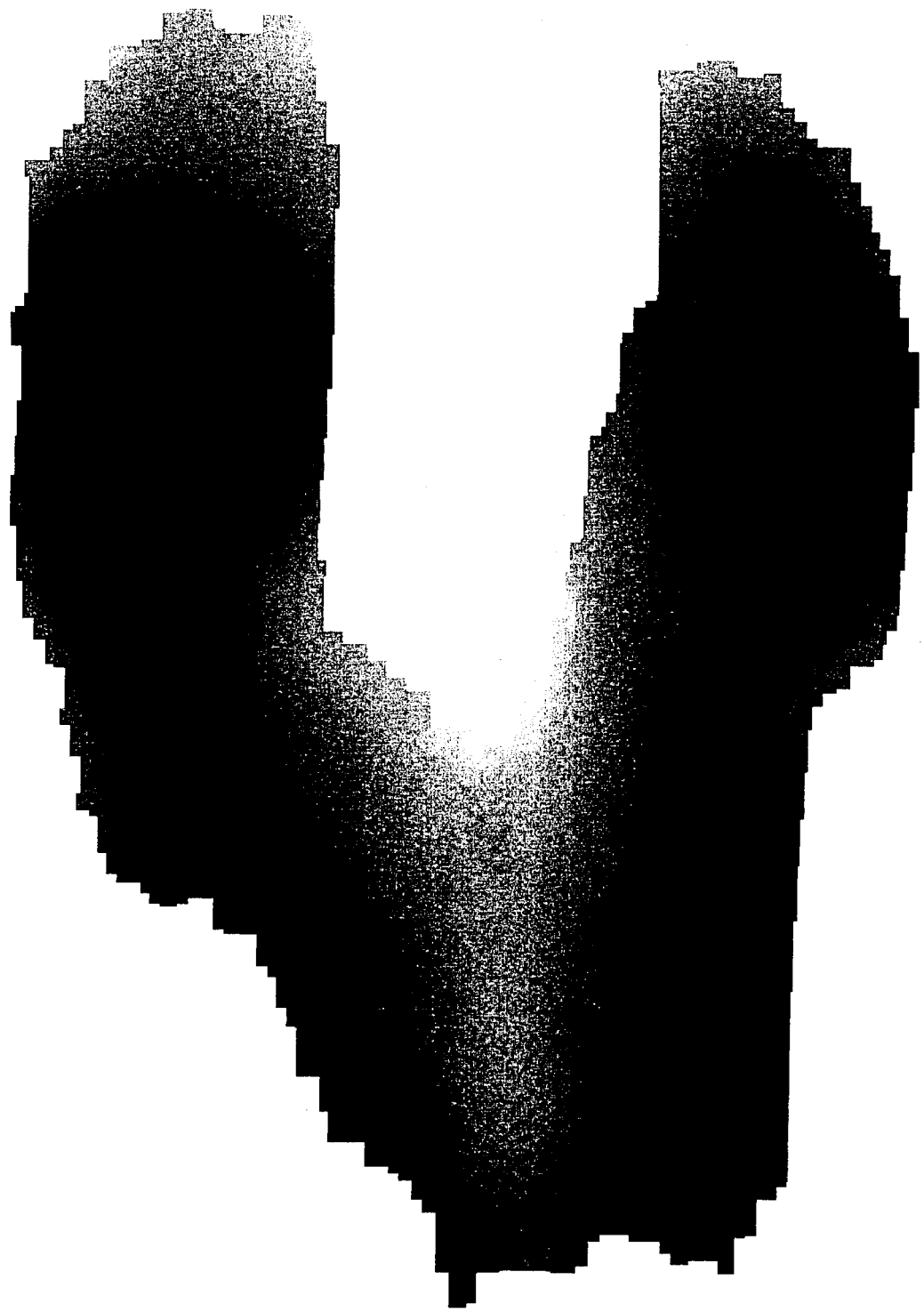

The grid resolution is adjusted to match the MRI image slice resolution. Because of the uneven spacing between contour points projected on the grid, a-Gaussian interpolation technique is applied on the resulting offset image to fill the gaps (see FIGS. 9(a) and 9(b)). A similar offset map representation for the cartilage-synovium interface is obtained by projecting the contour points from the cartilage-synovium interface on the same biparametric surface grid used for the bone (step 54).

The new biparametric representation includes much of the information present in the three-dimensional representation, but has reduced processing requirements. Because it is two-dimensional, it can be efficiently displayed on conventional monitors. The biparametric view also represents a relatively standardized view of the joint, and it is contemplated that such views could be compared for different patients qualitatively or quantitatively to determine patterns of disease progression for patients or groups of patients.

Figure 10:
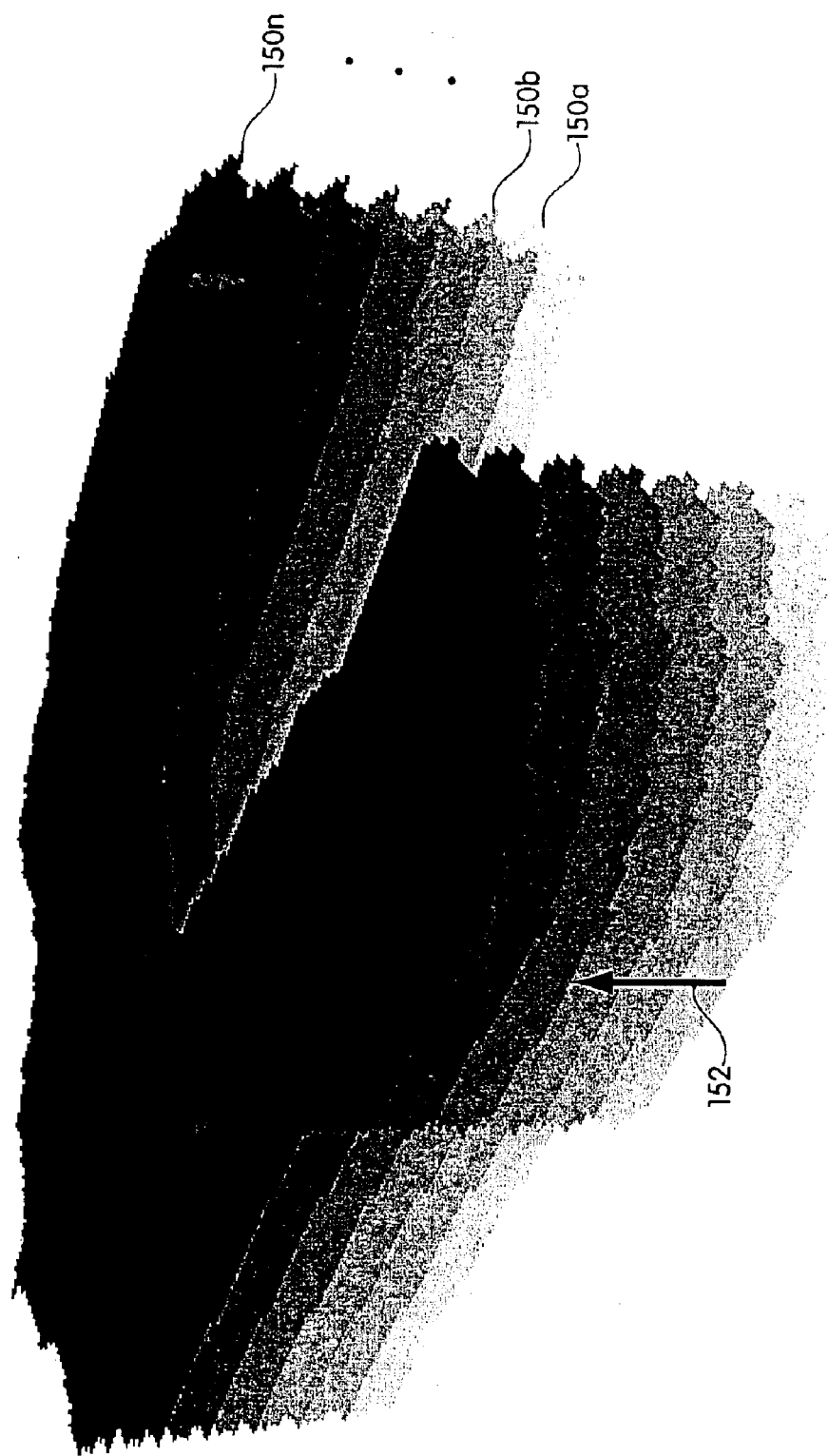
FIG. 10 is a perspective diagram illustrating the generation by the system of FIG. 1 of new three-dimensional cartilage images.

Referring to FIG. 10, the system obtains new images of the cartilage based on the biparametric surface coordinate systems derived for the data (step 56). This process results in a layered representation of the cartilage that is akin to the structure of an onion. Each cartilage slice 150a, 150b . . . 150n presents the intensity image obtained by extracting all pixels located at an isometric distance 152 from the bone surface. The operator can move through these slices, allowing him or her to see the effects of the disease on different levels of the bone and cartilage.

The sub-pixel accuracy processing module 28 uses these new three-dimensional images and the offset image map of the bone surface to obtain a three-dimensional sub-pixel representation of the bone surface. This process improves the accuracy of the first image surfaces and subsequent operations performed on them.

The signal analysis module 36 also applies two signal processing methods (step 60) to the new three-dimensional images (from step 56). The first of these is a textural analysis of the cartilage pixel organization in the cartilage slices (from step 56). The second is local signal density analysis of the cartilage that can be displayed as a "cartilage radiograph" used to find local hypo-signal regions.

The system then generates a display mapping for the cartilage (step 62). For comparison purposes, the cartilage is mainly represented by two maps. The first is a volume image map where each pixel represents a local volume localized on a 300 micron×300 micron surface, and the second is a thickness image map where each pixel represents a local mean thickness localized on a 300 micron×300 micron surface. A third map is used as a mask map that defines one or more topo-anatomical regions. This mask map is uses to obtain local thickness or volume.

Figure 11:
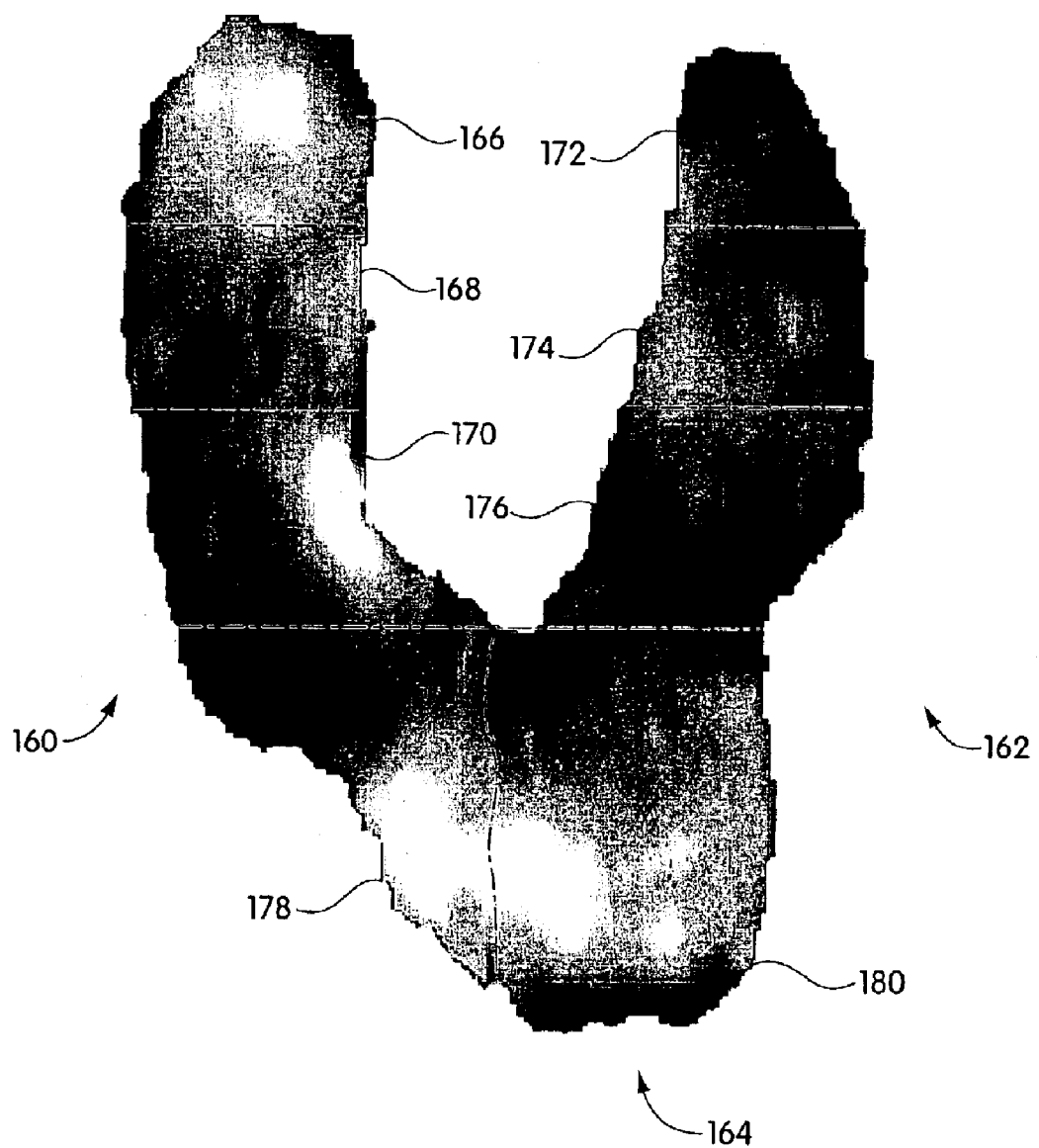
FIG. 11 is a diagram illustrating the breakdown of a femoral cartilage image into sub-regions.

Different structures within a joint can be quantified separately using the mask map. For example, the knee can be broken into anterior, central, and posterior areas of the tibial medial plateau, and medial, central, and lateral areas of the tibial lateral plateau. Posterior, central, and anterior areas of the femoral medial and lateral condyles could also be quantified, as could the patella. Different type of masks that have a topological and anatomical meaning can be easily tailored to the application to represent new specific region. An example to illustrate this process is the Bull-eyes mask used to represent four specific regions applied on the Tibial cartilage volume and thickness maps (FIG. 11). By separating these regions, a physician may be able to glean a more precise understanding of the progression of the disease.

Other attributes of the three dimensional data can also be derived. Physical characteristics of the cartilage that affect the quality of the MRI image signal, such as density or microstructural properties, can be mapped to colors. These properties may provide valuable diagnostic information about disease progression.

These three maps and the maps generated by the signal analysis module can be evaluated in a number of ways. They can be displayed on a monitor of a workstation from a viewpoint defined by a skilled operator, such as a radiologist, who can qualitatively evaluate them. They can also be transformed into other forms, such as an estimated thickness histogram.

After an appropriate interval, such as six months, a follow-up examination takes place. During this examination, an operator places the patient in the same position that he occupied during his initial examination (step 64) and obtains the same type of imaging data (step 66). Phantom data for the system may also be obtained (step 68).

The system then repositions the bone surface within the second image data set to match the position of the bone surface in the first data set (step 70). This process begins with a manual bone surface positioning in three planes (sagital, coronal, axial) with suitable interactive interface. This interface allows the user to move the bone surface with six degrees of freedom (three rotation controls and three translation controls) to obtain a first approximation of the surface position.

The rest of the procedure is performed automatically, and uses the manually obtained approximate surface position as initialization parameter. During this part of the process, the bone surface is precisely fitted by least square distance minimization between surface points and corresponding three-dimensional image edges. The repositioning operations for the bone also result in a repositioning of the cartilage. The bone surface is used as a reference for the repositioning because it is expected that the bone surface will normally not globally change the cartilage surface.

This process is performed by a robust least square minimization of the difference in combination with a surface filtering of the new image data to the sub-pixel level. Once the bone biparametric surface has been fitted in the new MR image sets of the same patient, the new Cartilage-synovium interface is segmented in a manner that is similar to the first cartilage segmentation step. A new biparametric surface can then be derived for the deformation of the cartilage (step 72). The data set resulting from this step expresses the difference between the two surfaces.

The system can then map the new data into one of the formats described above, such as a volume or thickness map (step 74). These maps can be then be combined with their earlier counterparts to generate a difference mapping (step 76). The difference mapping can then be displayed (step 78).

Referring to FIGS. 11–14, the system can also derive results for different regions of an anatomical feature. The contours of these regions can be based on anatomical principles or on the observation of symptoms from results for earlier acquisitions. Different regions may also be monitored for different conditions or different patients, so that the results obtained correlate as closely as possible with the progression or state of the condition being monitored.

Figure 12A:
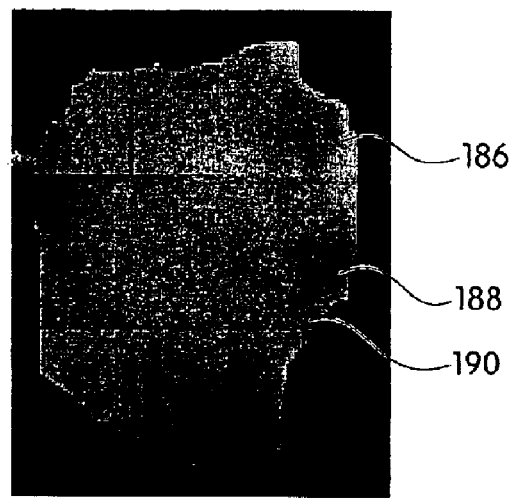
FIG. 12A is a diagram illustrating the breakdown of a medial tibial cartilage image into transversal sub-regions.
Figure 12B:
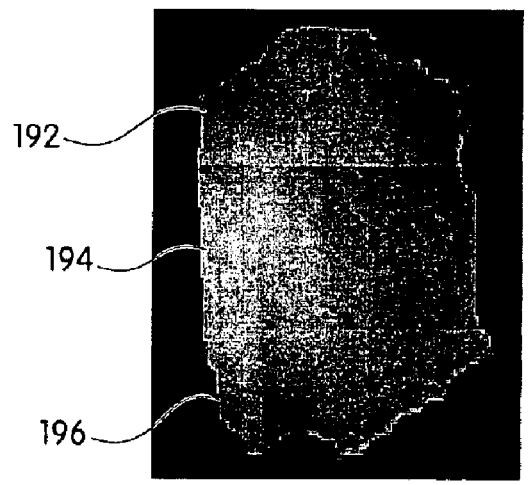
FIG. 12B is a diagram illustrating the breakdown of a lateral tibial cartilage image into transversal sub-regions.
Figure 13A:
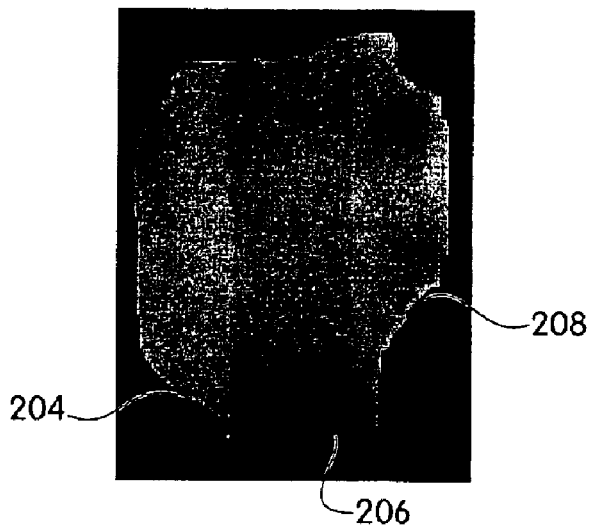
FIG. 13A is a diagram illustrating the breakdown of a medial tibial cartilage image into sagital sub-regions.
Figure 13B:
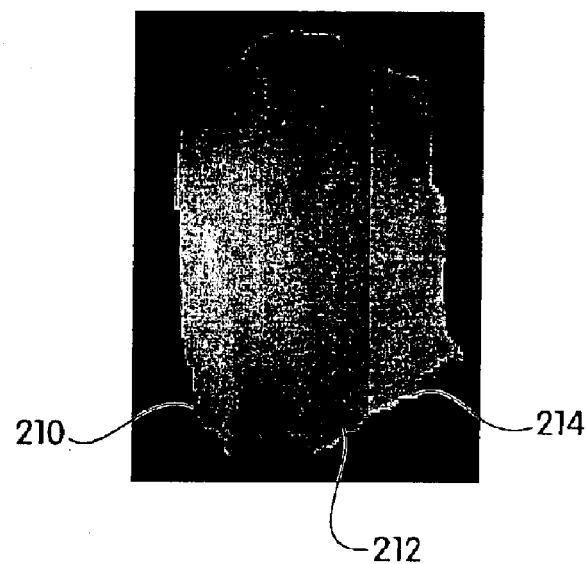
FIG. 13B is a diagram illustrating the breakdown of a lateral tibial cartilage image into sagital sub-regions.

The regions can be broken down based on Cartesian or polar coordinates. As shown in FIG. 11, for example, the femoral cartilage 164 can be divided according to Cartesian coordinates into a medial condyle area 160, a lateral condyle area 162, and a patelar area 164. The medial condyle and lateral condyle areas can be further subdivided into posterior areas (166, 172), central areas (168, 174) and anterior areas (170, 176), and the patelar area can be further subdivided into a medial area 178 and a lateral area 180. As shown in FIGS. 12–13, the tibial cartilage can be represented as a thickness map, as a medial region 182 that is transversally divided into a number of sub regions 186, 188, 190, or as a lateral region 184 that is transversally divided into a number of sub regions 192, 194, 196. The tibial cartilage can also be represented as a medial region 200 that is sagitally divided into a number of sub regions 204, 206, 208, or a lateral region 202 that is sagitally divided into a number of sub regions 210, 212, 212.

Figure 14A:
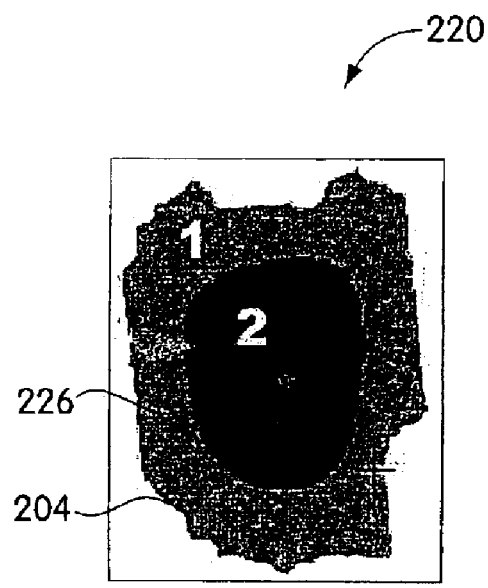
FIG. 14A is a diagram illustrating the breakdown of a medial tibial cartilage image into concentric sub-regions.
Figure 14B:
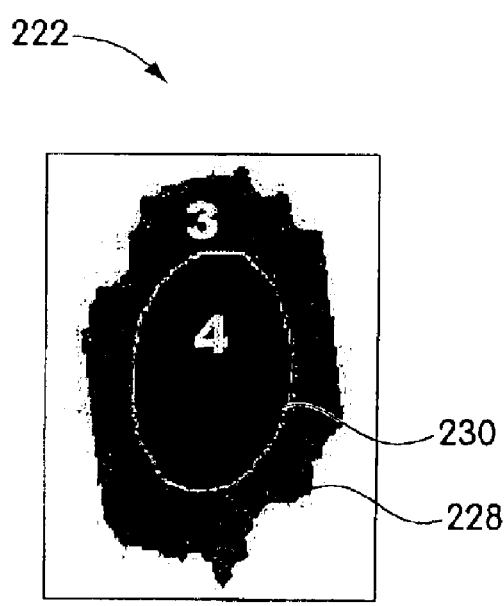
FIG. 14B is a diagram illustrating the breakdown of a lateral tibial cartilage image into concentric sub-regions.

As shown in FIG. 14, for example, the tibial cartilage can be divided according to polar coordinates into a "bull's-eye" representation. A medial slice 220 can be divided into one or more concentric rings 224 that surround a central area 226. Similarly, a lateral slice 222 can be divided into one or more concentric rings 228 that surround a central area 230.

EXAMPLE 1

Fifteen patients with knee osteoarthritis were recruited from outpatient rheumatology clinics. These patients included male and female individuals satisfying American College of Rheumatologists (ACR) criteria for primary osteoarthritis. They were each symptomatic and required treatment.

In all cases there was radiological evidence of osteoarthritis in the affected knee, including an X-ray within six months. Each patient exhibited a minimal grade two severity on either space narrowing, osteophyte and/or sclerosis on the Kellgren and Lawrence scale. Absence of chondrocalcinosis was required, and patients with end-stage radiological disease (i.e., grade four) or isolated femoropateilar osteoarthritis were not included in the study.

Patients were ruled out on the basis of a number of possibly confounding conditions, including secondary osteoarthrits, inflammatory arthritis, post-traumatic arthritis, metabolic arthritis, septic arthritis, crystal-induced disease, Paget's disease of the bone, avascular necrosis, or neurogenic arthritis. Previous corticoid injections in the study knee within the last three months or systemic corticoid use for any other reason were also grounds for exclusion. Ruled out as well were patients with severe (i.e., class IV) functional disability and candidates for imminent knee joint surgery, or patients with contralateral total joint replacement.

In the presence of bilateral symptomatic knees, the patient would choose the most symptomatic knee to be studied. In the case of similar symptoms for both knees, the toss of a coin would determine which one would be injected and studied. The patient's informed consent was required before admission into the study. A clinical evaluation of the patients, using validated measures, was also performed at baseline, six months and twelve months.

The patients were assessed at baseline, six months, and one year using an MRI system generally comparable to that described above. As part of this assessment, the images obtained were systematically analyzed and quantified using a processing system generally comparable to that described above. Each MRI acquisition was repeated by a different technician on the same day.

The total cartilage volume was calculated for each of the fifteen patients. The resulting volume values computed for the same-day tests were correlated using a Sperman's Rank test. The significance of the overall cartilage volume changes for the fifteen patients was evaluated using a Wilcoxon-signed rank test at six months and one year.

The correlation coefficient for the same day acquisitions was consistently found to be close to 0.99 with a p value well in excess of 0.05. These results indicate that the technique exhibits a very high degree of repeatability in its measurements of cartilage volume. Preliminary 18 months results for global and topographical changes in cartilage volume and thickness are promising and further analysis of these results is in progress.

EXAMPLE 2

Thirty-five patients with knee osteoarthritis were recruited from outpatient rheumatology clinics using similar criteria to those used for the first Example. The patients exhibited the baseline demographics presented in table 1.

TABLE 1

| Age (yrs.) | 63.1 (9.1) | Womac Pain | 59.4 (3.93) |
|---|---|---|---|
| % female | 74% | Wornac Stiff. | 45.7 (4.77) |
| Weight (kg) | 84.1 (15.1) | Womac Fnct. | 60.3 (3.99) |
| % Analg. | 82.6% | Womac Total | 56.9 (3.99) |
| % NSAIDs | 77% | Patient Global | 54.5 (3.74) |
| | | SF-36 PCS | 37.1 (1.65) |
| 50 Walk (sec) | 11.6 (3.6) | VAS PAIN | 48.2 (4.97) |
| ROM (deg.) | 126.9 (12.2) | MD Global | 59.8 (3.12) |

(VAS scores 100 = worst)

The patients were assessed at baseline, six months, and one year using an MRI system generally comparable to that described above. As part of this assessment, the images obtained were systematically analyzed and quantified using a processing system generally comparable to that described above. Imaging parameters were: Voxel size: 0.3×0.4×1 mm, with a 512×410 grid; 3D FISP; TR=42, and TE=7.

The total cartilage volume was calculated for each of the thirty-five patients. Paired t-tests were computed for the 6-month data and an analysis of variance (ANOVA) for multiple measurements was performed for the 12-month data. The results are presented in Table 2.

TABLE 2

| MRI Location | Mean (s.e.m.) Median | t-value | p-value* |
|---|---|---|---|
| At 6 months: n = 35 | | | |
| Medial Condyle | −3.34 (0.96) −2.12 | −3.48 | 0.001 |
| Lateral Condyle | −2.11 (0.48) −1.99 | −4.35 | 0.0001 |
| Medial Compart. | −2.11 (0.65) −1.41 | −3.27 | 0.002 |
| Lateral Compart. | −1.62 (0.39) −1.65 | −4.09 | 0.0001 |
| Global | −1.81 (0.43) −1.49 | −4.23 | 0.0001 |
| At 12 months: n = 34 | | | |
| Medial Condyle | −5.03 (1.33) −2.39 | −3.79 | 0.001 |
| Lateral Condyle | −2.65 (0.76) −2.46 | −3.49 | 0.001 |
| Medial Compart. | −3.91 (1.41) −1.84 | −2.77 | 0.009 |
| Lateral Compart. | −1.78 (0.56) −1.36 | −3.17 | 0.003 |
| Global | −2.38 (0.51) −1.50 | −4.64 | 0.0001 |

*Paired t-test for 6-month data.
ANOVA for 12-month data.

Correlation coefficients for the cartilage volume losses against clinical parameter changes were computed, and are presented in Table 3.

TABLE 3

| WOMAC | Month 6 | Month 12 |
|---|---|---|
| Pain | −0.025 | −0.086 |
| Stiffness | −0.000 | −0.070 |
| Function | +0.145 | +0.030 |
| VAS pain | +0.189 | −0.032 |
| Pt Global | +0.038 | +0.071 |
| MD Global | +0.206 | +0.290 |
| SF36 Physical Funct. | +0.110 | +0.220 |
| SF36 General Health | +0.077 | −0.058 | p-values = all ns.

Treatment efficacy power calculations (alpha=0.05, beta=0.80) were performed, and the results are presented in Table 4.

TABLE 4

| Using the expected Internal-Compartment Volume loss: | |
|---|---|
| −20% Difference at 1 year: | N = 216 |
| −30% Difference at 1 year: | N = 97 |
| −40% Difference at 1 year: | N = 55 |
| Using the expected Global-Cartilage Volume loss: | |
| −20% Difference at 1 year: | N = 412 |
| −30% Difference at 1 year: | N = 184 |
| −40% Difference at 1 year: | N = 104 |

These results are quite promising. They indicate that cartilage volume losses are detectable and are statistically significant at 6 months and 1 year. Further analyses are needed, however, to establish the correlation of the cartilage losses with the clinical parameters. Nonetheless, the tool should be useful to evaluate the progression of knee osteoarthritis and the therapeutic efficacy of "chondroprotective" agents in clinical trials.

The present invention has now been described in connection with a number of specific embodiments thereof. However, numerous modifications which are contemplated as falling within the scope of the present invention should now be apparent to those skilled in the art. For example, the techniques described may be used in veterinary applications or for the imaging of other types of structures in the body. Therefore, it is intended that the scope of the present invention be limited only by the scope of the claims appended hereto. In addition, the order of presentation of the claims should not be construed to limit the scope of any particular term in the claims.

What is claimed is:

1. An orthopedic magnetic resonance imaging system, comprising:
   a source of magnetic resonance imaging data sets resulting from successive magnetic resonance imaging acquisitions from a diseased joint of a patient, wherein the source of magnetic resonance imaging data sets includes a magnetic resonance imaging system and a support assembly operative to immobilize the diseased joint within the magnetic resonance imaging system with the joint at a predetermined three-dimensional position,
   a segmentation module responsive to the source of magnetic resonance imaging data sets and operative to segment surfaces in the joint based on information contained within at least one of the data sets,
   a registration module responsive to the source of magnetic resonance imaging data sets and operative to spatially register, in three dimensions, information represented by a first of the data sets with respect to information represented by one or more further data sets for the same patient, and
   a comparison module responsive to the registration module and operative to detect differences between information represented by the data sets caused by progression of the disease in the joint of the patient between acquisitions.

2. The apparatus of claim 1 wherein the magnetic resonance imaging system includes a knee coil and wherein the support assembly includes a heel constraint and at least two flexible wedges that are each operative to interact with a leg of the patient and the knee coil.

3. An orthopedic magnetic resonance imaging system, comprising:
   a source of magnetic resonance imaging data resulting from magnetic resonance imaging acquisitions from a joint of a patient,
   segmentation result storage, and
   a segmentation module that is responsive to the source of magnetic resonance imaging data and to the segmentation result storage, and that is operative to detect a boundary between two anatomical features of the joint in three dimensions based on both three-dimensional information from the joint of the patient and prior segmentation results stored in the segmentation result storage.

4. The apparatus of claim 3 further including a registration module responsive to the source of magnetic resonance imaging data and operative to spatially register three-dimensional image data from a first acquisition for the patient and three-dimensional image data from a later acquisition for the same patient.

5. An orthopedic magnetic resonance imaging system, comprising:
   a source of magnetic resonance imaging data resulting from magnetic resonance imaging acquisitions from a diseased joint of a patient, and
   a segmentation module that is responsive to the source of magnetic resonance imaging data sets and is operative to detect a boundary between two anatomical features of the joint in three dimensions by detecting an outline in each of a plurality of at least generally parallel planes within the volume, wherein the outline in at least some of the planes is based on data from at least one other of the planes.

6. A method of monitoring disease progression in a joint, comprising:

obtaining a first magnetic resonance imaging data set resulting from magnetic resonance imaging acquisition of a joint of a patient, and segmenting an outline of a boundary between two anatomical features of the joint of the patient in three dimensions by detecting an outline in each of a plurality of at least generally parallel planes within the volume, wherein the outline in at least some of the planes is based on data from at least one other of the planes.

7. The method of claim 6 wherein the steps of obtaining and segmenting are applied to a medical patient.

8. The method of claim 6 wherein the steps of obtaining and segmenting are applied to a veterinary patient.

9. An orthopedic magnetic resonance imaging system, comprising:

means for obtaining a first magnetic resonance imaging data set resulting from magnetic resonance imaging acquisition of a joint of a patient, and means for segmenting an outline of a boundary between two anatomical features of the joint of the patient in three dimensions by detecting an outline in each of a plurality of at least generally parallel planes within the volume, wherein the outline in at least some of the planes is based on data from at least one other of the planes.

10. A method of monitoring disease progression in a joint, comprising:

obtaining a first magnetic resonance imaging data set resulting from magnetic resonance imaging acquisition of a joint of a patient, delineating joint features in the first magnetic resonance imaging data set, obtaining a second magnetic resonance imaging data set resulting from a magnetic resonance imaging acquisition of the same joint for the same patient after the step of obtaining a first magnetic resonance imaging data set, delineating joint features in the second magnetic resonance imaging data set, spatially registering joint features delineated in the first magnetic resonance imaging data set and joint features delineated in the second magnetic resonance imaging data set, detecting differences between the spatially registered data sets for the patient, and evaluating the effects of one or more pharmaceutical agents on the patient based on results of the step of comparing.

11. The method of claim 10 wherein the steps of obtaining and spatially registering are applied to a medical patient.

12. The method of claim 10 wherein the steps of obtaining and spatially registering are applied to a veterinary patient.

13. The method of claim 10 wherein the step of evaluating is applied for a pharmaceutical agent designed to treat rheumatic diseases affecting the cartilage.

14. A method of monitoring disease progression in a joint, comprising:

obtaining a first magnetic resonance imaging data set resulting from magnetic resonance imaging acquisition of a joint of a patient, delineating joint features in the first magnetic resonance imaging data set, obtaining a second magnetic resonance imaging data set resulting from a magnetic resonance imaging acquisition of the same joint for the same patient after the step of obtaining a first magnetic resonance imaging data set, delineating joint features in the second magnetic resonance imaging data set, spatially registering joint features delineated in the first magnetic resonance imaging data set and joint features delineated in the second magnetic resonance imaging data set, detecting differences between the spatially registered data sets for the patient, and determining how to treat the patient based on results of the step of comparing.

15. A method of monitoring disease progression in a joint, comprising:

obtaining a first magnetic resonance imaging data set resulting from magnetic resonance imaging acquisition of a joint of a patient, delineating joint features in the first magnetic resonance imaging data set, obtaining a second magnetic resonance imaging data set resulting from a magnetic resonance imaging acquisition of the same joint for the same patient after the step of obtaining a first magnetic resonance imaging data set, delineating joint features in the second magnetic resonance imaging data set, spatially registering joint features delineated in the first magnetic resonance imaging data set and joint features delineated in the second magnetic resonance imaging data set, detecting differences between the spatially registered data sets for the patient, and administering treatment delivery for the patient based on results of the step of comparing.

16. The apparatus of claim 15 wherein the step of obtaining a first magnetic resonance imaging data set obtains a baseline magnetic resonance imaging data set.

* * * * *